United States Patent [19]

Kern et al.

[11] Patent Number: 5,925,615
[45] Date of Patent: Jul. 20, 1999

[54] **AWAPUHI (*ZINGIBER ZERUMBET*) - CONTAINING HAIR CLEANSING AND CONDITIONING COMPOSITIONS**

[75] Inventors: Dale G. Kern, Hyde Park; Janet Faye Lephart, Orem, both of Utah

[73] Assignee: Nu Skin International, Inc., Provo, Utah

[21] Appl. No.: 09/036,531

[22] Filed: Mar. 6, 1998

Related U.S. Application Data

[51] Int. Cl.$^6$ .............................. C11D 3/38; C11D 7/045; C11D 7/50; A61K 7/06
[52] U.S. Cl. ..................... 510/463; 510/119; 510/130; 424/74
[58] Field of Search ................... 510/119, 130, 510/463; 424/74

[56] References Cited

U.S. PATENT DOCUMENTS 5,597,557  1/1997  Kumar et al. ..................... 424/70.17
5,826,546  10/1998  Epstein ............................. 119/651

OTHER PUBLICATIONS

Govindarajan, V.S., Ginger—Chemistry, Technology, and Quality Evaluation: Part 2, Critical Reviews in Food Science and Nutrition, (1982) 17 (3) 189–258, 1982.

Olatunji, O.A., "The Structure and Development of Stomata in Some Zingiberales," Notes from the Royal Botanic Garden Edinburgh, vol. 38, (3) 499–516, 1980.

Oliveros, M.B., et al., "Pharmagcognostic Studies on *Zingiber zerumbet* (Linne) Smith and its Proposed Variety (Family Ziniberaceae)," Int. J. Crude Drug Res. 20 (3) 1982. 141–153, 1982.

Varma, S.K., et al., "Chemotaxonomy of Zingiberales 1: Genus *Zingiber Boehmer*," Proc. Natl. Acad. Sci. India, Section B (Biological Sciences) 61 (B) IV, 1991. 445–449.

"Tome Hawaiian Awapuhi Shampoo . . . ," Product Alert, Jan. 17, V.24, No.3, 1994.

"Mr. Michael's Salon Formula Shampoo . . . Tropical Blend Shampoo (compare with Paul Mitchell Awapuhi) . . . ," Product Alert, Aug. 24, 1992, V.22, No.34.

"Cream Rinses & Conditioners," Product Alert, Jul. 25, 1988, V.18, No.30.

"Freeman . . . Hawaiian Ginger Shampoo . . . extracts . . . ," Product Alert, Sep. 7, 1992, V.22, No. 36.

Carroll, M., "Shopping Honolulu (Special Section: The Hawaiian Islands)," Sales & Marketing Management (Successful Meeting/Jun. 1993), V.145, No. 6, 35–38.

*Primary Examiner*—Alan Diamond
*Assistant Examiner*—John M. Petruncio
*Attorney, Agent, or Firm*—Thorpe, North & Western, L.L.P.

[57] ABSTRACT

A cleansing and conditioning shampoo composition is described that contains an extract of shampoo ginger or awapuhi, *Zingiber zerumbet*. Other ingredients include water, surfactants, conditioning agents, thickening agents, stabilizers, preservatives, pH adjusting agents, fragrance, and color. Methods of use and methods of making the shampoo composition are also described. A hair conditioner composition and methods of making and using thereof are also described. The hair conditioner composition contains awapuhi extract, a conditioning agent, an emulsion stabilizer, an anti-static agent, a preservative, and water.

60 Claims, No Drawings

AWAPUHI (*ZINGIBER ZERUMBET*) - CONTAINING HAIR CLEANSING AND CONDITIONING COMPOSITIONS

BACKGROUND OF THE INVENTION

This invention relates to hair cleansing and conditioning compositions and methods of making and using thereof. More particularly, the invention relates to hair cleansing and conditioning compositions that incorporate herbal extracts.

Herbal extracts are widely known and used in the art of making shampoos and hair conditioners. Herbal extracts are used for a variety of reasons, and are chosen based on their particular properties. For example, some herbal extracts are chosen and incorporated into shampoos and conditioners because of the fragrance they add to the composition. Additionally, other herbal extracts are chosen because of the advantageous effects they may have on the health of the hair by reducing dryness, increasing its body, or making it shine.

The word "awapuhi" is the general Hawaiian term used in reference to all ginger plants. There are many different types of awapuhi, such as awapuhi ke'oke'o or white ginger, awapuhi melemele or yellow ginger, awapuhi'ula'ula, or red ginger, and finally, awapuhi kuahiwi, which is know as "shampoo ginger" or by the Latin binomial *Zingiber zerumbet*. Each type of ginger has different properties that make it suitable for different uses. For example, white ginger is extremely aromatic, red ginger has edible roots and has been incorporated into many traditional Hawaiian meals, and *Zingiber zerumbet* has become known for both its fragrant qualities and its ability to clean and condition hair when used as a shampoo. Other gingers have been used by native healers as remedies for all sorts of ailments, from toothaches to upset stomachs.

To date, there are several types of shampoos on the market that incorporate an "awapuhi extract." Paul Mitchell, Kava, and Jason's Natural shampoos all list an awapuhi extract as an ingredient, and most of them specify that the type of awapuhi used is a white ginger. Some of the others use a red or yellow ginger, but none of them incorporate an extract from *Zingiber zerumbet*. Most of these shampoos have incorporated the ginger for its "tropical scent," and some have even been criticized for not living up to their advertisements. For example, Paula Begoun, a noted beauty aid analyst, criticized Paul Mitchell's Awapuhi Shampoo stating that the Awapuhi in that shampoo "has little effect on the hair." She then continued to say that over time the shampoo can actually build up on the hair and weigh it down.

Additionally, even though the Hawaiian people have long used *Zingiber zerumbet* for various uses, including squeezing the juice directly onto their hair during bathing, the herb has yet to be incorporated into a commercially produced shampoo that contains many of the other ingredients typically found in shampoos on the market today. Because of its unique hair cleansing and conditioning properties, the incorporation of the *Zingiber zerumbet* extract into a shampoo formulation to create a combination hair cleansing and conditioning composition would represent a great advancement over the prior art.

BRIEF SUMMARY OF THE INVENTION

It is an object of the present invention to provide a hair cleansing and conditioning composition.

It is also an object of the present invention to provide a hair cleansing and conditioning composition that contains a *Zingiber zerumbet* extract.

It is another object of the invention to provide a hair conditioner composition that contains an extract of *Zingiber zerumbet*.

These and other objects can be realized by providing a composition comprising a *Zingiber zerumbet* extract and one or more other ingredients useful in a shampoo such as, but not limited to, one or more surfactants, one or more conditioning agents, a thickening agent, a stabilizing ingredient, a preservative ingredient, a pH adjusting ingredient, and water. Additionally, the shampoo composition may optionally contain a fragrance ingredient, and a coloring ingredient.

The surfactant of the present invention may be a combination of several surfactants that have different properties and functions, such as cleansing and foam boosting. Additionally, the conditioner of the present invention may include a combination of several conditioners, each having different properties that contribute to the moisturization, body, control, and overall health and manageability of the hair.

The present invention also encompasses a method of cleansing and conditioning hair by first wetting the hair, then applying the hair cleansing and conditioning composition, agitating the hair cleansing and conditioning composition throughout the hair, and finally, rinsing the hair cleansing and conditioning composition out of the hair. By using the composition of the present invention in this manner, greater hair cleansing and conditioning results are obtained. These cleansing and conditioning results are important, as they affect the hair's overall health and appearance.

The invention also relates to a hair conditioning composition containing about 0.5 to 10.0% of *Zingiber zerumbet* extract; about 3 to 23% of a conditioning agent; about 0.5 to 4% of an emulsion stabilizer; about 0.0008 to 0.5% of a preservative; about 0.05 to 6% of an anti-static agent; and about 56.5 to 95.9% of water.

DETAILED DESCRIPTION

Before the present compositions and method for making and using thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a surfactant" includes a mixture of two or more of such surfactants, reference to "a thickener" includes reference to one or more of such thickeners, and reference to "a conditioner" includes reference to a mixture of two or more of such conditioners.

In describing and claiming the present invention, the following terminology will be used in accordance with the definitions set out below.

As used herein, "awapuhi kuahiwi," "avapuhi extract," "ava puhi moni," and "shampoo ginger" mean extracts of the bracts of *Zingiber zerumbet* (L.) Smith. As described above, other products, loosely termed "awapuhi," have been used in shampoos and similar personal care formulations, but such formulations are extracted from roots of the red or torch ginger, yellow ginger, or white ginger (*Hedycium coronariom* Keonig).

A shampoo composition according to the present invention for cleansing and conditioning hair comprises in percentage by weight:

a) about 0.5 to 10% *Zingiber zerumbet* extract;
b) about 25 to 40% surfactant;
c) about 3 to 5% conditioning agent;
d) about 0.05 to 2.0% thickening agent;
e) about 42.8 to 71.4% water;
f) about 0.00020 to 0.1% of a stabilizing ingredient;
g) about 0.00010 to 0.5% of a preservative ingredient; and
h) about 0.0005 to 0.800 percent of a pH adjusting ingredient.

Optionally, the composition can further comprise a fragrance ingredient in an amount of about 0.01 to 1.5% by weight and/or a coloring ingredient in an amount of about 0.0002 to 0.1500% by weight.

The surfactant can comprise a cleansing agent, a foam boosting agent, or mixtures thereof. Illustrative cleansing agents include alkyl glucosides, alkyl ether sulfates, alkyl sulfates, and mixtures thereof.

In a preferred embodiment, the shampoo composition includes an alkyl glucoside in an amount of 8 to 20% by weight, wherein the alkyl glucoside is a member selected from the group consisting of lauryl glucoside, decyl glucoside, and mixtures thereof.

In another preferred embodiment, the shampoo composition includes an alkyl ether sulfate in an amount of 2 to 12% by weight, wherein the alkyl ether sulfate is a member selected from the group consisting of sodium laureth sulfate, ammonium laureth sulfate, magnesium laureth sulfate, and mixtures thereof.

In still another preferred embodiment, the shampoo composition includes an alkyl sulfate in an amount of 8 to 20% by weight, wherein the alkyl sulfate is a member selected from the group consisting of sodium lauryl sulfate, ammonium lauryl sulfate, magnesium lauryl sulfate, and mixtures thereof.

Illustrative foam boosting surfactants include alkanolamides, and quaternized alkyl or substituted alkyl derivatives of N,N-dimethyl glycine, and mixtures thereof.

In a preferred embodiment, the shampoo composition includes an alkanolamide in an amount of 1 to 5% by weight, wherein the alkanolamide is a member selected from the group consisting of acetamide MEA, cocamide DEA, lauramide DEA, and mixtures thereof.

In another preferred embodiment, the shampoo composition includes a quaternized alkyl or substituted alkyl derivative of N,N-dimethyl glycine in an amount of 1 to 4% by weight, wherein such quaternized alkyl or substituted alkyl derivative of N,N-dimethyl glycine is selected from the group consisting of cocamidopropyl betaine, lauryl hydroxysultaine, and mixtures thereof.

Illustrative conditioning agents for use in the present invention include glyceryl esters, dimethylsiloxanes, aliphatic alcohols, alkoxylated carboxylic acids, and mixtures thereof.

Preferably, the shampoo composition includes a glyceryl ester in an amount of 0.5 to 5.0% by weight, wherein the glyceryl ester is a member selected from the group consisting of polyglyceryl-10 decaoleate, polyglyceryl-6 distearate, polyglyceryl-6 oleate, polyglyceryl-6 hexaoleate, polyglyceryl-10 stearate, and mixtures thereof.

It is also preferred that the shampoo composition comprise a dimethylsiloxane in an amount of 0.3 to 2.0% by weight, wherein the dimethylsiloxane is a member selected from the group consisting of dimethicone copolyol, dimethiconol, phenyl trimethicone, and mixtures thereof.

It is further preferred that the shampoo composition contain an aliphatic alcohol in an amount of 0.05 to 4.0% by weight, wherein such aliphatic alcohol is a member selected from the group consisting of proplyene glycol, butylene glycol, panthenol, phytantriol, and mixtures thereof.

It is still further preferred that the shampoo composition comprise an alkoxylated carboxylic acid in an amount of 0.1 to 3.0% by weight, wherein the alkoxylated carboxylic acid is a member selected from the group consisting of jojoba wax PEG-80 esters, jojoba wax PEG-120 esters, PEG-100 stearate, PEG-120 distearate, PEG-150 distearate, PEG-175 distearate, and mixtures thereof.

Illustrative thickening agents that can be used according to the present invention include carbohydrates such as guar hydroxypropyltrimonium chloride, hydroxypropylmethylcellulose, maraya (*Sterculia urens*) gum, methylcellulose, xanthan gum, and mixtures thereof. In preferred embodiments, the thickening agent is present in an amount of 0.1 to 1.0% by weight.

Illustrative preservatives that are suitable for use according to the present invention include methylparaben, proplyparaben, methylchloroisothiazolinone, methylisothiazolinone, diazolidinyl urea, and mixtures thereof. Preferably, the preservative is present in an amount from 0.0003 to 0.5% by weight.

The shampoo composition should also contain a pH adjusting ingredient for adjusting the pH of the composition to the preferred range of about pH 5.0 to 7.0. Illustrative pH adjusting ingredients include buffers, acids, bases, and mixtures thereof, which are well known in the art. A preferred pH adjusting ingredient comprises citric acid.

It is also preferred that the shampoo composition contain a stabilizing ingredient comprising chlorophyllin-copper complex. Preferred amounts are in the range of about 0.0002 to 0.0040% by weight.

The shampoo composition is made by mixing the selected ingredients together in the appropriate amounts, and then packaging the finished product in an appropriate container.

The composition is used for cleansing and conditioning hair by the steps of wetting the hair, applying a selected amount of the cleansing and conditioning composition to the hair, agitating the hair cleansing and conditioning composition throughout the hair, and rinsing the hair cleansing and conditioning composition from the hair.

Method of Preparing *Zingiber zerumbet* Extract

Bracts of *Zingiber zerumbet* (L.) Smith, more commonly known as awapuhi kuahiwi or shampoo ginger or native wild shampoo ginger, are collected during flowering time. Harvesting of the bracts is done when either (a) the bract is at least 5 cm in length and bearing at least two flowers or (b) the bract is reddish in color, indicating full maturity. The bracts are removed by cutting the bract stem about 2 cm below the bract.

As soon as possible after harvesting, bracts are stored at about 4° C. to preserve the mucilaginous material contained in the bracts and protect such material from deterioration. Between steps of the extraction procedure, the mucilaginous material or extract is likewise refrigerated.

In one illustrative first step of the extraction procedure, the harvested bracts are pressed in a press at about 1 ton of pressure. The mucilage is collected, which also contains some bract pieces of about 2 cm in diameter as well as smaller particulates. This mucilage is then passed through a 10-mesh stainless steel screen to remove larger particles including bract pieces.

In another illustrative first step of the extraction procedure, the harvested bracts are subjected to low speed centrifugation (about 100–400 rpm) until the clear slimy juice or mucilage ceases to flow from the bracts. This mucilage is collected. Passage through a sieve is not usually necessary because the mucilage collected in this manner does not usually contain large particulates.

Immediately following the initial extraction step, whether by pressing or by centrifugation, the mucilage is mixed with a preservative and a cation chelating agent. In an illustrative embodiment of this step, phenoxyethanol is added to 0.4% (w/w), diazolidinyl urea is added to 0.6% (w/w), and disodium EDTA is added to 0.1% (w/w), and then the preservatives and chelating agent are mixed with the extract. It has been discovered that omission of the chelating agent results in formation of a dark-colored precipitate after storage of the extract containing the preservatives.

Following addition of a preservative and a chelating agent, it is advantageous to remove additional particulate contaminants that remain in the extract. This can be carried out by centrifugation at 10,000 to 15,000 rpm in a centrifugal filtration unit equipped with a 60-mesh screen. The retentate containing particulate matter larger than 60-mesh is then discarded. The filtrate is then subjected to further centrifugal filtration through a 100-mesh screen. The retentate, containing particles greater than 100-mesh, is discarded. The resulting filtrate is the final extract.

This extract can be purchased commercially from Oils of Aloha (Waialua, HI; catalog no. Awapuhi K997).

EXAMPLE 1

In this example, awapuhi extract prepared according to the present invention was subjected to laboratory analysis by an independent analytical laboratory, Irvine Analytical Laboratories, Inc. (Irvine, Calif.), to determine the amounts of certain elements, carbohydrates, fats, proteins, and the like. The results obtained for 3 separate lots are shown in Table 1.

TABLE 1

| Analysis | Lot 1[a] | Lot 2 | Lot 3 | Method |
|---|---|---|---|---|
| Calcium | 3.6 mg | 3.5 mg | 2.8 mg | ICP[b] |
| Iron | 0.19 mg | 0.12 mg | 0.11 mg | ICP |
| Potassium | 16.5 mg | 19.2 mg | 21.8 mg | ICP |
| Sodium | 20 mg | 20 mg | 19 mg | ICP |
| Total Sugars | 0.17 g | 0.17 g | 0.17 g | HPLC[c], AOAC 980.13 |
| Fat | 0.025 g | 0.04 g | 0.01 g | AOAC 922.06[d] |
| Protein | 0.70 g | 0.61 g | 1.1 g | Leco |
| Calories | 3 Cal | 2 Cal | 4.0 Cal | Calculation |
| Carbohydrates | <0.1 g | <0.1 g | <0.1 g | Calculation |
| Moisture | 99.2 g | 99.3 g | 99.2 g | AOAC 920.10 |
| Ash | 0.05 g | 0.05 g | 0.04 g | AOAC 923.03 |

[a]All amounts are per 100 g of extract.
[b]Inductively coupled plasma
[c]High pressure liquid chromatography
[d]Acid hydrolyzed

EXAMPLE 2

In this example, a sample of awapuhi extract according to the present invention was subjected to analysis for heavy metals and vitamin C by an independent testing laboratory, Irvine Analytical Laboratories, Inc. The results showed that the extract contained <10 ppm of heavy metals (USP 23<231> (through Sup. 7)) and 4.17 g/100 g of vitamin C (AOAC 967.21).

EXAMPLE 3

In this example, there is described a shampoo performance test. The materials tested were as follows: (a) a conditioning shampoo according to the present invention containing 10% *Zingiber zerumbet* extract (hereinafter, "conditioning shampoo"), (b) a control conditioning shampoo identical to the *Zingiber zerumbet*-extract-containing shampoo except that it contained no *Zingiber zerumbet* extract (hereinafter, "control shampoo"), and (c) a leading commercially available shampoo containing unknown amounts of *Zingiber officinalis* (edible ginger) extract (hereinafter, "commercial shampoo"). Test shampoo solutions were prepared from each of these three shampoos by preparing 2% (v/v) solutions in water.

Lather height was tested using the cylinder method of J. Ross & G. D. Miles, 18 Oil Soap 99 (1941), hereby incorporated by reference. Ten ml of each shampoo test solution was placed in a clean, dry 50-ml graduated cylinder. Each cylinder was inverted 25 times, then the height of the foam was measured. The results of this test are summarized in Table 2.

TABLE 2

| Product | Total Foam (ml) |
|---|---|
| Conditioning Shampoo | 22 |
| Control Shampoo | 18 |
| Commercial Shampoo | 16 |

The greater the volume of foam, the better the foaming properties of the shampoo formulation. This example shows that the conditioning shampoo according to the present invention exhibits superior foaming properties as compared to either the control shampoo that differs only by lacking awapuhi extract or the commercially available shampoo containing an extract of the edible ginger, *Zingiber officinalis*.

EXAMPLE 4

In this example, shampoo test solutions were prepared according to the procedure of Example 3. Lather drainage was tested according to method of J. R. Hart & M. T. DeGeorge, 184 Drug Cosmetic Industry 46 (1984), hereby incorporated by reference. Briefly, 150 ml of each shampoo test solution was placed in a blender and then blended for 20 seconds at the high speed setting. Then, 1 gram of the resulting lather was placed in the center of a paper towel. The distance that water traveled outward after 10 minutes was measured. The shorter the distance that water traveled, the denser and thicker the lather. The longer the distance the water traveled, the thinner the lather. High shear rates produced by a blender are considered more like that obtained on hair under actual shampoo conditions. The results of this test is shown in Table 3.

TABLE 3

| Product | Total Distance (cm/10 min) |
|---|---|
| Conditioning Shampoo | 3.3 |
| Control Shampoo | 4.1 |
| Commercial Shampoo | 5.2 |

These results show that the awapuhi-containing conditioning shampoo according to the present invention produces a thicker lather than either the control shampoo lacking awapuhi extract or the commercially available shampoo containing an extract of edible ginger, *Zingiber officinalis*.

EXAMPLE 5

In this example, the test shampoo solutions of Example 3 were tested for lather feel. Lather was prepared according to the method described in Example 4. Multiple observers subjectively rated these lathers for texture and flexibility. In the texture test, a score of 1 represented lacy and loosely packed bubbles, and a score of 5 represented tiny and densely packed bubbles. In the flexibility test, a score of 1 indicated lather that easily deformed on touch, whereas a score of 5 indicated a lather that was judged bouncy and that easily restored its shape on touch. Thus, in both tests, the higher the numeric value, the better the chance that a consumer would like the shampoo. The results of these tests are shown in Tables 4 and 5.

TABLE 4

| Product | Judge 1 | Judge 2 | Judge 3 | Average |
|---|---|---|---|---|
| Conditioning Shampoo | 4 | 5 | 5 | 4.7 |
| Control Shampoo | 5 | 4 | 4 | 4.3 |
| Commercial Shampoo | 2 | 3 | 2 | 2.3 |

TABLE 5

| Product | Judge 1 | Judge 2 | Judge 3 | Average |
|---|---|---|---|---|
| Conditioning Shampoo | 4 | 5 | 5 | 4.7 |
| Control Shampoo | 4 | 4 | 4 | 4.0 |
| Commercial Shampoo | 3 | 2 | 2 | 2.3 |

These results show that the awapuhi-containing shampoo according to the present invention rates higher than either the control shampoo lacking awapuhi extract or the commercially available shampoo containing an extract of edible ginger, *Zingiber officinalis*, for both texture and flexibility of the foam, which are considered desirable characteristics of a shampoo product.

EXAMPLE 6

In this example, the cleaning ability of the test shampoo solutions prepared according to the procedure of Example 3 were tested. Synthetic sebum was prepared according to the following formula: 20% (v/v) olive oil, 10% (v/v) palmitic acid, 10% (v/v) stearic acid, 10% (v/v) oleic acid, 10% (v/v) paraffin wax, 5% (v/v) squalene, and 15% (v/v) spermaceti. A 5% (v/v) synthetic sebum solution was prepared in ethanol. Three sets of 15 Japanese hair swatches per set were prepared. Each swatch was approximately one centimeter in width and 10 cm in length. Each swatch was weighed, and the sample weight was recorded. Each swatch was then treated with the 5% synthetic sebum solution and dried. Each sample was then weighed again such that the mass of synthetic sebum on each swatch could be determined. Five hundred ml of each test shampoo solution was prepared according to the procedure of Example 3. Each set of swatches was then submerged in a test shampoo solution and washed for 2 minutes, rinsed in water for 1 minute, and dried overnight in a drying oven. The swatches were then weighed again such that the mass of contaminant removed from each swatch could be determined. The average amount of synthetic sebum on each swatch and average amount of contaminant removed from each swatch are summarized for each treatment in Table 6.

TABLE 6

| Product | Sebum (mg) | Removed (mg) | Cleansing % |
|---|---|---|---|
| Conditioning Shampoo | 84 | 116 | 138 |
| Control Shampoo | 134 | 140 | 104 |
| Commercial Shampoo | 58 | 50 | 86 |

These results show that the conditioning shampoo according to the present invention and the control shampoo not only removed the synthetic sebum placed on the hair, but also removed pre-existing unknown contaminants that were on the hair. Thus, the conditioning shampoo and the control shampoo were effective in removing the synthetic sebum, but the conditioning shampoo according to the present invention was clearly superior for its cleansing ability. The commercial shampoo did not remove all of the synthetic sebum placed on the hair, and thus could not be considered efficient for thorough cleansing of the hair.

EXAMPLE 7

In this example there are shown illustrative formulations of the conditioning shampoo according to the present invention, wherein all amounts are presented in percent by weight.

| Formulation A | |
|---|---|
| Water | 49.58% |
| Ammonium lauryl sulfate | 15.0% |
| Decyl glucoside | 12.0% |
| Ava puhi (Zingiber zerumbet) extract | 10.0% |
| Sodium laureth sulfate | 4.5% |
| Polyglyceryl-6-distearate | 3.0% |
| Cocamide DEA | 2.68% |
| Cocamidopropyl betaine | 1.5% |
| Dimethiconol | 1.0% |
| Fragrance | 0.4% |
| Guar hydroxypropyltrimonium chloride | 0.2% |
| Panthenol | 0.1% |
| Citric acid | 0.03% |
| Methylchloroisothiazolinone | 0.00081% |
| Chlorophyllin-copper complex | 0.00040% |
| Methylisothiazolinone | 0.00025% |
| Formulation B | |
| Water | 45.69% |
| Magnesium lauryl sulfate | 12.0% |
| Lauryl glucoside | 15.0% |
| Ava puhi (Zingiber zerumbet) extract | 10.0% |
| Ammonium laureth sulfate | 8.0% |
| Polyglyceryl-10-decaoleate | 3.0% |
| Acetamide MEA | 2.50% |
| Lauryl hydroxysultaine | 1.50% |
| Dimethicone copolyol | 1.0% |
| Fragrance | 0.38% |
| Hydroxypropylmethylcellulose | 0.2% |
| Propylene glycol | 0.1% |
| Citric acid | 0.03% |
| Methylparaben | 0.5% |
| Chlorophyllin-copper complex | 0.00060% |
| Formulation C | |
| Water | 59.10% |
| Ava puhi (Zingiber zerumbet) extract | 10.0% |
| Lauryl glucoside | 4.0% |
| Decyl glucoside | 4.0% |
| Sodium laureth sulfate | 2.0% |
| Ammonium laureth sulfate | 2.0% |
| Sodium lauryl sulfate | 4.0% |
| Ammonium lauryl sulfate | 4.0% |
| Polyglyceryl-6 oleate | 1.5% |
| Polyglyceryl-6 hexaoleate | 1.5% |

-continued

| | |
|---|---|
| Cocamide DEA | 1.75% |
| Lauramide DEA | 1.25% |
| Cocamidopropyl betaine | 0.5% |
| Lauryl hydroxysultaine | 0.5% |
| Dimethiconol | 0.3% |
| Phenyl trimethicone | 0.3% |
| Methylcellulose | 0.1% |
| Xanthan gum | 0.1% |
| Butylene glycol | 1.0% |
| Phytantriol | 1.0% |
| PEG-100 stearate | 0.1% |
| Propylparaben | 0.5% |
| Citric acid | 0.8% |
| Chlorophyllin-copper complex | 0.0002% |
| Formulation D | |
| Water | 59.4% |
| Ava puhi (Zingiber zerumbet) extract | 5.0% |
| Decyl glucoside | 20.0% |
| Polyglyceryl-10 stearate | 1.25% |
| Lauramide DEA | 5.0% |
| Cocamidopropyl betaine | 4.0% |
| Dimethiconol | 1.0% |
| Karaya gum | 1.0% |
| Panthenol | 1.25% |
| Jojoba wax PEG-120 esters | 1.5% |
| Diazolidinyl urea | 0.3% |
| Citric acid | 0.2% |
| Chlorophyllin-copper complex | 0.1% |
| Formulation E | |
| Water | 53.40% |
| Ava puhi (Zingiber zerumbet) extract | 10.0% |
| Lauryl glucoside | 10.3% |
| Ammonium laureth sulfate | 2.2% |
| Ammonium lauryl sulfate | 10.6% |
| Polyglyceryl-6 distearate | 2.6% |
| Acetamide MEA | 4.7% |
| Lauryl hydroxysultaine | 1.1% |
| Cocamidopropyl betaine | 2.0% |
| Phenyl trimethicone | 0.35% |
| Guar hydroxypropyltrimonium chloride | 0.64% |
| Propylene glycol | 0.7% |
| PEG-100 stearate | 1.0% |
| Methylchloroisothazolinone | 0.002% |
| Methylisothiazolinone | 0.0005% |
| Fragrance | 0.22% |
| Color | 0.15% |
| Citric acid | 0.03% |
| Chlorophyllin-copper complex | 0.0002% |
| Formulation F | |
| Water | 59.18% |
| Decyl glucoside | 20% |
| Sodium lauryl sulfate | 10% |
| Lauramide DEA | 5% |
| Polyglyceryl-10 stearate | 3% |
| Hydroxypropylmethylcellulose | 1% |
| Methylparaben | 0.25% |
| Propylparaben | 0.25% |
| Phytantriol | 0.4% |
| PEG-150 distearate | 0.4% |
| Fragrance | 0.4% |
| Color | 0.1% |
| Citric acid | 0.02% |
| Chlorophyllin-copper complex | 0.0005% |

The present invention also relates to a hair conditioner containing an extract of *Zingiber zerumbet*. Such hair conditioner composition comprises the following ingredients, wherein all percentages are by weight:

(a) about 0.5 to 10.0% of *Zingiber zerumbet* extract;
(b) about 3 to 23% of a conditioning agent;
(c) about 0.5 to 4% of an emulsion stabilizer;
(d) about 0.0008 to 0.5% of a preservative;
(e) about 0.05 to 6% of an anti-static agent; and
(f) about 56.5 to 95.9% of water.

The hair conditioner composition can further comprise other optional ingredients that are advantageous to such a product, such as fragrance, stabilizers, colors, pH adjusting agents, and the like. For example, in one illustrative embodiment the hair conditioner composition can comprise about 0.01 to 1.5% by weight of fragrance, about 0.0002 to 0.15% by weight of color, about 0.001 to 0.5% by weight of pH adjusting agent, and/or about 0.0004 to 0.1% of a stabilizer.

Conditioning agents that can be used in the present invention include those conditioning agents that are well known in the art, including dimethylsiloxanes, synthetic polymers, aliphatic alcohols, quaternary ammonium salts, and mixtures thereof.

In a preferred embodiment, the hair conditioner composition includes a dimethylsiloxane in an amount of about 2 to 8% by weight, wherein the dimethylsiloxane is a member selected from the group consisting of dimethicone, cyclomethicone, phenyl trimethicone, dimethicone copolyol, and mixtures thereof.

In another preferred embodiment, the hair conditioner composition includes a synthetic polymer in an amount of about 1 to 5% by weight, wherein the synthetic polymer is a member selected from the group consisting of polydecene, acrylamide copolymers, acrylate/$C_{10-30}$ alkyl acrylate crosspolymers, and mixtures thereof.

In still another preferred embodiment, the hair conditioner composition includes an aliphatic alcohol in an amount of about 0.05 to 4% by weight, wherein the aliphatic alcohol is a member selected from the group consisting of propylene glycol, butylene glycol, panthenol, phytantriol, and mixtures thereof.

In yet another preferred embodiment, the hair conditioner composition includes a quaternary ammonium salt in an amount of about 0.05 to 6% by weight, wherein the quaternary ammonium salt is a member selected from the group consisting of stearalkonium chloride, behenyltrimonium chloride, behentrimonium methosulfate, benzalkonium chloride, cetrimonium chloride, cetrimonium bromide, tricetylmonium chloride, polyquaternium-10, and mixtures thereof.

Emulsion stabilizers that can be used in the present invention include those emulsion stabilizers that are well known in the art, including fatty organic alcohols. In a preferred embodiment of the hair conditioning composition, the emulsion stabilizer is present in an amount of about 0.5 to 4% by weight, wherein such emulsion stabilizer is a fatty organic alcohol selected from the group consisting of cetyl alcohol and stearyl alcohol.

Anti-static agents that can be used in the present invention include those anti-static agents that are well known in the art, including quaternary ammonium salts. In a preferred embodiment of the present invention, the anti-static agent is present in an amount of about 0.05 to 6% by weight, wherein such anti-static agent is a quaternary ammonium salt selected from the group consisting of stearalkonium chloride, behenyltrimonium chloride, behentrimonium methosulfate, benzalkonium chloride, cetrimonium chloride, cetrimonium bromide, tricetylmonium chloride, polyquaternium-10, and mixtures thereof.

Preservatives that can be used in the present invention include those preservatives that are well known in the art. In a preferred embodiment of the invention, the preservative is present in an amount of about 0.0008 to 0.5% by weight, wherein such preservative is a member selected from the group consisting of methylparaben, propylparaben, methylchloroisothiazolinone, methylisothiazolinone, diazolidinyl urea, and mixtures thereof.

Fragrances, colors, pH adjusting agents, and stabilizers that can be used in the present invention include those compounds that are well known in the art for such purposes. For example, pH adjusting agents can include buffers, acids, bases, and mixtures thereof, depending on the pH adjustment that is desired. A preferred pH range for the present hair conditioning composition is about pH 3.5–5.5. A preferred pH adjusting agent in the present invention is citric acid. By way of further example, a preferred stabilizer is chlorophyllin-copper complex, which also provides color to the composition.

The hair conditioner composition is made by mixing and emulsifying the ingredients. The composition can then be packaged in an appropriate container.

The hair conditioner composition is used for conditioning hair as follows. As a preliminary step, the hair is washed and rinsed, preferably with the awa puhi-containing conditioning shampoo described herein. While the hair is wet, a selected amount of the hair conditioner composition is applied to the hair and thoroughly massaged into the hair. Optionally, the composition can then be permitted to remain in contact with the hair momentarily, for example for 2–5 minutes. Finally, the hair conditioner composition is rinsed from the hair.

EXAMPLE 8

In this example there are shown illustrative formulations of the hair conditioner composition according to the present invention, wherein all amounts are presented in percent by weight.

| Formulation 1 | |
| --- | --- |
| Water | 74.0184% |
| Ava puhi (Zingiber zerumbet) extract | 10.0% |
| dimethicone | 3.0% |
| polydecene | 3.0% |
| cyclomethicone | 2.0% |
| propylene glycol | 2.0% |
| cetyl alcohol | 2.0% |
| stearalkonium chloride | 1.0% |
| stearyl alcohol | 1.0% |
| panthenol | 1.0% |
| fragrance | 0.5% |
| methylparaben | 0.2% |
| behenyltrimonium chloride | 0.2% |
| propylparaben | 0.08% |
| methylchloroisothiazolinone | 0.0009% |
| chlorophyllin-copper complex | 0.0004% |
| methylisothiazolinone | 0.0003% |
| Formulation 2 | |
| Water | 75.4% |
| Ava puhi (Zingiber zerumbet) extract | 10.0% |
| phenyl trimethicone | 3.0% |
| dimethicone copolyol | 2.0% |
| acrylamide copolymers | 3.0% |
| butylene glycol | 2.0% |
| phytantriol | 1.0% |
| cetyl alcohol | 1.0% |
| stearyl alcohol | 1.0% |
| benzalkonium chloride | 0.5% |
| fragrance | 0.5% |
| diazolidinyl urea | 0.3% |
| methylparaben | 0.2% |
| chlorophyllin-copper complex | 0.1% |
| Formulation 3 | |
| Water | 95.9% |
| Ava puhi (Zingiber zerumbet) extract | 0.5% |
| dimethicone | 3.0% |
| cetyl alcohol | 0.5% |
| cetrimonium bromide | 0.05% |
| methylisothiazolinone | 0.0003% |

| Formulation 4 | |
| --- | --- |
| Water | 60.9% |
| Ava puhi (Zingiber zerumbet) extract | 10.0% |
| Dimethicone | 4.0% |
| Dimethicone Copolyol | 4.0% |
| polydecene | 2.5% |
| acrylamide copolymer | 2.5% |
| propylene glycol | 1.0% |
| butylene glycol | 1.0% |
| panthenol | 1.0% |
| phytantriol | 1.0% |
| behentrimonium methosulfate | 1.5% |
| cetrimonium chloride | 1.5% |
| tricetylmonium chloride | 1.5% |
| polyquaternium-10 | 1.5% |
| cetyl alcohol | 2.0% |
| stearyl alcohol | 2.0% |
| methylparaben | 0.25% |
| propylparaben | 0.25% |
| fragrance | 1.0% |
| chlorophyllin-copper complex | 0.1% |
| citric acid | 0.5% |

We claim:

1. A shampoo composition for cleansing and conditioning hair comprising in percentage by weight:
   (a) about 0.5 to 10% *Zingiber zerumbet* extract;
   (b) about 25 to 40% surfactant;
   (c) about 3 to 5% conditioning agent;
   (d) about 0.05 to 2.0% thickening agent;
   (e) about 42.8 to 71.4% water;
   (f) about 0.00020 to 0.1% of a stabilizing ingredient;
   (g) about 0.00010 to 0.5% of a preservative ingredient; and
   (h) about 0.0005 to 0.800% of a pH adjusting ingredient.

2. The shampoo composition of claim 1 further comprising a fragrance ingredient in an amount of about 0.01 to 1.5% by weight.

3. The shampoo composition of claim 1 further comprising a coloring ingredient in an amount of about 0.0002 to 0.1500% by weight.

4. The shampoo composition of claim 1 where in said surfactant comprises a cleansing agent, a foam boosting agent, or mixtures thereof.

5. The shampoo composition of claim 4 wherein said surfactant comprises a cleansing agent selected from the group consisting of alkyl glucosides, alkyl ether sulfates, alkyl sulfates, and mixtures thereof.

6. The shampoo composition of claim 5 wherein said alkyl glucoside is present in an amount of 8 to 20% by weight and is a member selected from the group consisting of lauryl glucoside, decyl glucoside, and mixtures thereof.

7. The shampoo composition of claim 5 wherein said alkyl ether sulfate is present in an amount of 2 to 12% by weight and is a member selected from the group consisting of sodium laureth sulfate, ammonium laureth sulfate, magnesium laureth sulfate, and mixtures thereof.

8. The shampoo composition of claim 5 wherein said alkyl sulfate is present in an amount of 8 to 20% by weight and is a member selected from the group consisting of sodium lauryl sulfate, ammonium lauryl sulfate, magnesium lauryl sulfate, and mixtures thereof.

9. The shampoo composition of claim 4 wherein said surfactant comprises a foam boosting agent selected from the group consisting of alkanolamides, and quaternized alkyl or substituted alkyl derivatives of N,N-dimethyl glycine, and mixtures thereof.

10. The shampoo composition of claim 9 wherein said alkanolamide is present in an amount of 1 to 5% by weight and is a member selected from the group consisting of acetamide MEA, cocamide DEA, lauramide DEA, and mixtures thereof.

11. The shampoo composition of claim 9 wherein said quaternized alkyl or substituted alkyl derivative of N,N-dimethyl glycine is present in an amount of 1 to 4% by weight and is selected from the group consisting of cocamidopropyl betaine, lauryl hydroxysultaine, and mixtures thereof.

12. The shampoo composition of claim 1 wherein said conditioning agent is a member selected from the group consisting of glyceryl esters, dimethylsiloxanes, aliphatic alcohols, alkoxylated carboxylic acids, and mixtures thereof.

13. The shampoo composition of claim 12 wherein said glyceryl ester is present in an amount of 0.5 to 5.0% by weight and is a member selected from the group consisting of polyglycerly-10 decaoleate, polyglyceryl-6 distearate, polyglyceryl-6 oleate, polyglyceryl-6 hexaoleate, polyglyceryl-10 stearate, and mixtures thereof.

14. The shampoo composition of claim 12 wherein said dimethylsiloxane is present in an amount of 0.3 to 2.0% by weight, and is a member selected from the group consisting of dimethicone copolyol, dimethiconol, phenyl trimethicone, and mixtures thereof.

15. The shampoo composition of claim 12 wherein said aliphatic alcohol is present in an amount of 0.05 to 4.0% by weight and is a member selected from the group consisting of proplyene glycol, butylene glycol, panthenol, phytantriol, and mixtures thereof.

16. The shampoo composition of claim 12 wherein said alkoxylated carboxylic acid is present in an amount of 0.1 to 3.0% by weight, and is a member selected from the group consisting of jojoba wax PEG-80 esters, jojoba wax PEG-120 esters, PEG-100 stearate, PEG-120 distearate, PEG-150 distearate, PEG-175 distearate, and mixtures thereof.

17. The shampoo composition of claim 1 wherein said thickening agent comprises a carbohydrate.

18. The shampoo composition of claim 17 wherein said carbohydrate is present in an amount of 0.1 to 1.0% by weight, and is a member selected from the group consisting of guar hydroxyproplytrimonium chloride, hydroxypropylmethylcellulose, maraya (*Sterculia urens*) gum, methylcellulose, xanthan gum, and mixtures thereof.

19. The shampoo composition of claim 1 wherein said preservative ingredient is present in an amount from 0.0003 to 0.5% by weight, and is a member selected from the group consisting of methylparaben, proplyparaben, methylchloroisothiazolinone, methylisothiazolinone, diazolidinyl urea, and mixtures thereof.

20. The shampoo composition of claim 1 wherein said pH adjusting ingredient comprises citric acid.

21. The shampoo composition of claim 1 wherein said stabilizing ingredient comprises chlorophyllin-copper complex.

22. A method of cleansing and conditioning hair, comprising the steps of:
(a) wetting the hair;
(b) applying a hair cleansing and conditioning composition comprising in percentage by weight:
  (i) about 0.5 to 10% *Zingiber zerumbet* extract;
  (ii) about 25 to 40% surfactant;
  (iii) about 3 to 5% conditioning agent;
  (iv) about 0.05 to 2.0% thickening agent;
  (v) about 42.8 to 71.4% water;
  (vi) about 0.00020 to 0.1% of a stabilizing ingredient;
  (vii) about 0.00010 to 0.5% of a preservative ingredient; and
  (viii) about 0.0005 to 0.800% of a pH adjusting ingredient;
(c) agitating said hair cleansing and conditioning composition throughout the hair; and
(d) rinsing said hair cleansing and conditioning composition from the hair.

23. A method of making a shampoo composition for cleansing and conditioning hair comprising the step of mixing in percentage by weight:
(a) about 0.5 to 10% Zingiber zerumbet extract;
(b) about 25 to 40% surfactant;
(c) about 3 to 5% conditioning agent;
(d) about 0.05 to 2.0% thickening agent;
(e) about 42.8 to 71.4% water;
(f) about 0.00020 to 0.1% of a stabilizing ingredient;
(g) about 0.00010 to 0.5% of a preservative ingredient; and
(h) about 0.0005 to 0.800% of a pH adjusting ingredient.

24. The method of claim 23 wherein said shampoo composition further comprises a fragrance ingredient in an amount of about 0.01 to 1.5% by weight.

25. The method of claim 23 wherein said shampoo composition further comprises a coloring ingredient in an amount of about 0.0002 to 0.1500% by weight.

26. The method of claim 23 wherein said surfactant comprises a cleansing agent, a foam boosting agent, or mixtures thereof.

27. The method of claim 26 wherein said surfactant comprises a cleansing agent selected from the group consisting of alkyl glucosides, alkyl ether sulfates, alkyl sulfates, and mixtures thereof.

28. The method of claim 27 wherein said alkyl glucoside is present in an amount of 8 to 20% by weight and is a member selected from the group consisting of lauryl glucoside, decyl glucoside, and mixtures thereof.

29. The method of claim 27 wherein said alkyl ether sulfate is present in an amount of 2 to 12% by weight and is a member selected from the group consisting of sodium laureth sulfate, ammonium laureth sulfate, magnesium laureth sulfate, and mixtures thereof.

30. The method of claim 27 wherein said alkyl sulfate is present in an amount of 8 to 20% by weight and is a member selected from the group consisting of sodium lauryl sulfate, ammonium lauryl sulfate, magnesium lauryl sulfate, and mixtures thereof.

31. The method of claim 26 wherein said surfactant comprises a foam boosting agent selected from the group consisting of alkanolamides, and quaternized alkyl or substituted alkyl derivatives of N,N-dimethyl glycine, and mixtures thereof.

32. The method of claim 31 wherein said alkanolamide is present in an amount of 1 to 5% by weight and is a member selected from the group consisting of acetamide MEA, cocamide DEA, lauramide DEA, and mixtures thereof.

33. The method of claim 31 wherein said quaternized alkyl or substituted alkyl derivative of N,N-dimethyl glycine is present in an amount of 1 to 4% by weight and is selected from the group consisting of cocamidopropyl betaine, lauryl hydroxysultaine, and mixtures thereof.

34. The method of claim 23 wherein said conditioning agent is a member selected from the group consisting of glyceryl esters, dimethylsiloxanes, aliphatic alcohols, alkoxylated carboxylic acids, and mixtures thereof.

35. The method of claim 34 wherein said glyceryl ester is present in an amount of 0.5 to 5.0% by weight and is a member selected from the group consisting of polyglycerly-10 decaoleate, polyglyceryl-6 distearate, polyglyceryl-6 oleate, polyglycerly-6 hexaoleate, polyglyceryl-10 stearate, and mixtures thereof.

36. The method of claim 34 wherein said dimethylsiloxane is present in an amount of 0.3 to 2.0% by weight, and is a member selected from the group consisting of dimethicone copolyol, dimethiconol, phenyl trimethicone, and mixtures thereof.

37. The method of claim 34 wherein said aliphatic alcohol is present in an amount of 0.05 to 4.0% by weight and is a member selected from the group consisting of proplyene glycol, butylene glycol, panthenol, phytantriol, and mixtures thereof.

38. The method of claim 34 wherein said alkoxylated carboxylic acid is present in an amount of 0.1 to 3.0% by weight, and is a member selected from the group consisting of jojoba wax PEG-80 esters, jojoba wax PEG-120 esters, PEG-100 stearate, PEG-120 distearate, PEG-150 distearate, PEG-175 distearate, and mixtures thereof.

39. The method of claim 23 wherein said thickening agent comprises a carbohydrate.

40. The method of claim 39 wherein said carbohydrate is present in an amount of 0.1 to 1.0% by weight, and is a member selected from the group consisting of guar hydroxyproplytrimonium chloride, hydroxypropylmethylcellulose, maraya (*Sterculia urens*) gum, methylcellulose, xanthan gum, and mixtures thereof.

41. The method of claim 23 wherein said preservative ingredient is present in an amount from 0.0003 to 0.5% by weight, and is a member selected from the group consisting of methylparaben, proplyparaben, methylchloroisothiazolinone, methylisothiazolinone, diazolidinyl urea, and mixtures thereof.

42. The method of claim 23 wherein said pH adjusting ingredient comprises citric acid.

43. The method of claim 23 wherein said stabilizing ingredient comprises chlorophyllin-copper complex.

44. A hair conditioner composition comprising in percent by weight:
(a) about 0.5 to 10.0% of *Zingiber zerumbet* extract;
(b) about 3 to 23% of a conditioning agent;
(c) about 0.5 to 4% of an emulsion stabilizer;
(d) about 0.0008 to 0.5% of a preservative;
(e) about 0.05 to 6% of an anti-static agent; and
(f) about 56.5 to 95.9% of water.

45. The hair conditioner composition of claim 44 further comprising a member selected from the group consisting of about 0.01 to 1.5% by weight of fragrance, about 0.0002 to 0.15% by weight of color, about 0.001 to 0.5% by weight of pH adjusting agent, and about 0.0004 to 0.1% of a stabilizer.

46. The hair conditioner composition of claim 45 wherein said pH adjusting agent is a member selected from the group consisting of buffers, acids, bases, and mixtures thereof.

47. The hair conditioner composition of claim 46 wherein said pH adjusting agent comprises citric acid.

48. The hair conditioner composition of claim 45 wherein said stabilizer comprises chlorophyllin-copper complex.

49. The hair conditioner composition of claim 44 wherein said conditioning agent is a member selected from the group consisting of dimethylsiloxanes, synthetic polymers, aliphatic alcohols, quaternary ammonium salts, and mixtures thereof.

50. The hair conditioner composition of claim 49 comprising 2 to 8% by weight of a dimethylsiloxane selected from the group consisting of dimethicone, cyclomethicone, phenyl trimethicone, dimethicone copolyol, and mixtures thereof.

51. The hair conditioner composition of claim 49 comprising about 1 to 5% by weight of a synthetic polymer selected from the group consisting of polydecene, acrylamide copolymers, acrylate/$C_{10-30}$ alkyl acrylate crosspolymers, and mixtures thereof.

52. The hair conditioner composition of claim 49 comprising about 0.05 to 4% by weight of an aliphatic alcohol selected from the group consisting of propylene glycol, butylene glycol, panthenol, phytantriol, and mixtures thereof.

53. The hair conditioner composition of claim 49 comprising about 0.05 to 6% by weight of a quaternary ammonium salt selected from the group consisting of stearalkonium chloride, behenyltrimonium chloride, behentrimonium methosulfate, benzalkonium chloride, cetrimonium chloride, cetrimonium bromide, tricetylmonium chloride, polyquaternium-10, and mixtures thereof.

54. The hair conditioner composition of claim 44 wherein said emulsion stabilizer is a fatty organic alcohol.

55. The hair conditioner composition of claim 54 wherein said fatty organic alcohol is a member selected from the group consisting of cetyl alcohol and stearyl alcohol.

56. The hair conditioner composition of claim 44 wherein said anti-static agent is a quaternary ammonium salt.

57. The hair conditioner composition of claim 56 wherein said quaternary ammonium salt is a member selected from the group consisting of stearalkonium chloride, behenyltrimonium chloride, behentrimonium methosulfate, benzalkonium chloride, cetrimonium chloride, cetrimonium bromide, tricetylmonium chloride, polyquaternium-10, and mixtures thereof.

58. The hair conditioner composition of claim 44 wherein said preservative is a member of the group consisting of methylparaben, propylparaben, methylchloroisothiazolinone, methylisothiazolinone, diazolidinyl urea, and mixtures thereof.

59. A method making a hair conditioner composition comprising mixing and emulsifying about 0.5 to 10.0% of *Zingiber zerumbet* extract; about 3 to 23% of a conditioning agent; about 0.5 to 4% of an emulsion stabilizer; about 0.0008 to 0.5% of a preservative; about 0.05 to 6% of an anti-static agent; and about 56.5 to 95.9% of water.

60. A method of using a hair conditioner composition for conditioning hair comprising the steps of:
(a) as a preliminary step, washing and rinsing the hair;
(b) then, while the hair is wet, applying a selected amount of the hair conditioner composition to the hair and thoroughly massaging the composition into the hair, wherein said composition comprises about 0.5 to 10.0% of *Zingiber zerumbet* extract; about 3 to 23% of a conditioning agent; about 0.5 to 4% of an emulsion stabilizer; about 0.0008 to 0.5% of a preservative; about 0.05 to 6% of an anti-static agent; and about 56.5 to 95.9% of water;
(c) rinsing the composition from the hair.

* * * * *